United States Patent [19]

Kraus

[11] Patent Number: 4,614,524

[45] Date of Patent: Sep. 30, 1986

[54] WATER-FREE HYDROCARBON SEPARATION MEMBRANE AND PROCESS

[75] Inventor: Menahem A. Kraus, St. Louis, Mo.

[73] Assignee: Monsanto Company, St. Louis, Mo.

[21] Appl. No.: 687,714

[22] Filed: Dec. 31, 1984

[51] Int. Cl.$^4$ ............................................. B01D 59/10
[52] U.S. Cl. ........................................ 55/16; 55/158; 210/638; 210/500.25
[58] Field of Search ................ 210/638, 500.2; 55/16, 55/158

[56] References Cited

U.S. PATENT DOCUMENTS 3,980,605  9/1976  Steigelmann et al. ................ 55/158
4,264,338  4/1981  Null .................................... 55/158

Primary Examiner—Frank Sever
Attorney, Agent, or Firm—R. L. Broad; Henry Croskell

[57] ABSTRACT

Water-free membranes suitable for separating aliphatically-unsaturated hydrocarbons from saturated hydrocarbons are disclosed wherein the membranes are comprised of preformed membranes of polymeric materials capable of chemically binding positive ions and the membranes have been ion exchanged to contain metal ions as well as being plasticized with polyhydric alcohols. The water-free membranes provide for facilitated transport of aliphatically-unsaturated hydrocarbons through a membrane process wherein the unsaturated species of the feed mixture is transported across the plasticized membrane by virtue of the metal ions interacting selectively and reversibly with the unsaturated species. The separation of ethylene from ethane utilizing the water-free membrane system is of particular interest.

11 Claims, No Drawings

WATER-FREE HYDROCARBON SEPARATION MEMBRANE AND PROCESS

BACKGROUND OF THE INVENTION

This invention relates to water-free separation membranes for separating aliphatically-unsaturated hydrocarbons from saturated hydrocarbons. In another aspect, the invention relates to a process for utilizing water-free membranes comprised of preformed membranes of polymeric material capable of chemically bonding positive metal ions wherein the membranes have been plasticized resulting from contacting of the preformed membranes with polyhydric alcohols. The invention is especially useful for separating ethylene from gaseous mixtures containing ethylene and other hydrocarbons, for example, ethane, methane and hydrogen in the absence of water.

Considerable commercial interest exists for separating various aliphatically-unsaturated hydrocarbons from mixtures of hydrocarbons. Aliphatically-unsaturated hydrocarbons are reactive materials that serve various roles in the chemical and hydrocarbon industry, generally as intermediates in chemical synthesis. A number of unsaturated hydrocarbons are employed as monomers in the formation of polymers and in this regard, olefins such as ethylene, propylene, butadiene and isoprene are well known. Aliphatic unsaturated hydrocarbons are most frequently available on a commercial basis in admixtures with other chemical compunds. These unsaturated hydrocarbon-containing streams are usually by-products of chemical synthesis or separation processes. When the hydrocarbon streams are liquid under normal conditions or can readily be liquified, ordinary distillation techniques are used to separate the hydrocarbon components provided they have sufficiently different boiling points for the process to be economically feasible. However, distillation may not be an attractive separation procedure when the hydrocarbon mixtures contain materials having close boiling points which is often the case with hydrocarbons of the same number of carbon atoms or having a difference of only one carbon atom. In these cases, different separation processes must be used which are frequently costly and involve operations such as solvent extraction, extraction distillation, cryogenics and the like.

When the aliphatically-unsaturated hydrocarbons and mixtures thereof with other similar boiling point hydrocarbons are in essentially the gaseous state at ambient temperatures and pressures, separation of the desired component from the mixture may be even more troublesome. In these situations, cryogenic processes may be used, however, frequently expense is prohibitive. These difficulties have created the need for use of semipermeable membranes for separating unsaturated hydrocarbons from saturated hydrocarbon mixtures.

Facilitated transport is a membrane process in which one species of a feed mixture is transported across a membrane preferentially by virtue of a component of the membrane interacting specifically and reversibly with that species. The facilitated aliphatically-unsaturated hydrocarbon transport process most thoroughly studied has been the separation of ethylene from its mixtures with saturated hydrocarbons. Unsaturated hydrocarbons have been known to interact with silver ions. The kinetics and equilibria of this reaction are such that it can be utilized to facilitate membrane transport. Use of metal ions, for example, silver ions has been taught for facilitated transport of unsaturated hydrocarbons; however, in all these teachings, the systems require water to both impregnate the membrane and to saturate the feed gas in order to prevent drying of the membrane. It is thought that the use of aqueous saturation is an absolute requirement for the success of the facilitated transport prooess, for example, the separation of ethylene from ethane. It is assumed that the reason for this need for the presence of water is that water acts as a solvent for the silver salts and/or as a plasticizer for the polymer matrix and/or provides the necessary electronic environment for the silver ion. The high volatility of water makes this requirement a major limitation to the process. Accidental drying of the membrane innerly irreversible destroys its separation capacity.

Combinations of liquid barrier permeation involving metal complexing techniques have been utilized in separating aliphatically-unsaturated hydrocarbons from mixtures of other hydrocarbon materials. These systems provide for a liquid barrier as a continuous, distinct or separate liquid phase adjacent to and in contact with a semipermeable film membrane which is relatively non-selective with respect to the passage of the components of the hydrocarbon feed mixture. In addition, systems are known which are directed to methods for separating various materials from mixtures of aliphatically-unsaturated hydrocarbons and other hydrocarbons involving the combined use of liquid barrier permeation and metal complexing techniques which exhibit selectivity for the unsaturated hydrocarbons. In these processes, the liquid barrier is an aqueous solution having dissolved therein metal ions which will complex with the component to be separated. The liquid barriers are employed in contact with semipermeable membranes which are essentially impermeable to the passage of the separation barrier. The selectivity and separation ability of these aqueous barrier, metal ion containing systems can be rendered ineffective over prolonged use due to the loss of water from the barrier membrane system. The selectivity and separation ability of these aqueous, metal ion membranes decreases upon drying, thus the need for addition of water, generally through mixture with the feedstream.

DEFINITIONS

For purposes of describing the invention, "polyhydric alcohols" are defined as compounds containing more than one hydroxyl groups, inclusive of monomeric and polymeric materials. Polyhydric alcohols can represent one or more mixtures of various polyhydric alcohols generally in fluid form under operating conditions.

The term "membrane" for purposes of this invention is defined as a preformed membrane of polymeric material capable of chemically binding positive metal ions and which is capable of being plasticized by polyhydric alcohols. These metal ion containing membranes are further capable of separating aliphatically plasticized unsaturated hydrocarbons from saturated hydrocarbon feedstocks without the presence of water either in the membrane or the feedstock.

"Metal ions" are hereby defined as positive ions capable of bonding with the polymers of the membrane which are pasticized by polyhydric alcohols and wherein the metal ions are capable of reversibly complexing with aliphatically-unsaturated hydrocarbons.

SUMMARY OF THE INVENTION

An object of the present invention is to provide a membrane and a process for separating aliphatically-unsaturated hydrocarbons from hydrocarbon mixtures wherein the membrane is water-free.

Another object of the present invention is to provide a permeable membrane system which is simpler to operate and less prone to failure due to the lack of dependence on water.

A further object of the invention is to provide polyhydric alcohol plasticized ion exchange membranes wherein metal ions are chemically bond to the polymeric materials of preformed membranes, and the membranes function selectively to permeate aliphatically-unsaturated hydrocarbons through reversibly complexing actions in a water free environment.

These objects are obtainable according to the present invention by ionically exchanging metal ions in a preformed polymeric membrane which is capable of binding metal ions to the polymers of the membrane wherein the membrane is plasticized by polyhydric alcohols either separately or in combination with the metal ionic exchange procedure. The resulting separation membranes are suitable for selectively permeating aliphatically-unsaturated hydrocarbons such as ethylene through the plasticized membrane and the actions of the metal ions bound to the polymeric materials of the membrane. The preformed membranes can be dense or asymmetric with dense zones which are comprised of polymeric materials which are capable of chemically binding positive ions and/or capable of being plasticized by polyhydric alcohols. The combination of the chemically bound positive ions, metal ions, and the plasticized preformed membrane produces a water-free membrane which is suitable for selectively permeating aliphatically-unsaturated hydrocarbons from saturated hydrocarbon mixtures.

The present invention provides a simple means to obviate the need for use of water in the separation membranes or the feed streams wherein aliphatically-unsaturated hydrocarbons are separated from saturated hydrocarbons. The separating membrane which is plasticized and chemically binds metal ions constitutes, for example, a dense membrane having substantial physical strength which is suitable for a variety of feed stock pressures and temperatures. In general, the preformed membrane is hydrophilic in nature; thus, the plasticization of the membrane by the polyhydric alcohols is throughout the thickness of the membrane as is the metal ion concentration. The preformed membrane having complete plasticization and metal ion distribution provides for complexing of the aliphatically-unsaturated hydrocarbons on contact by the feed stream with the membranes, permeation of the complex, followed by dissociation back to metal ion and the aliphatically-unsaturated hydrocarbon component of the complex on the permeate or discharge side of the membrane.

The novel features which are considered characteristic for the invention are set forth in particular in the appended claims. The invention itself, however, both as to its construction and its method of operation, together with additional objects and advantages thereof, will be best understood from the following description of specific embodiments.

DESCRIPTION OF THE PREFERRED EMBODIMENTS

Preformed, plasticized, metal ion containing membranes can be operated as water-free permeation membranes for the separation of aliphatically- unsaturated hydrocarbons from saturated hydrocarbons. For example, preformed ion exchange membranes can be ion exchanged wherein metal ions are introduced to the polymer of the preformed membrane which is followed by plasticization with polyhydric alcohols or can be accomplished in simultaneous treatments. The resulting plasticized, metal ion containing membranes include throughout the plasticized membrane, polyhydric alcohols and metal ions wherein the metal ions are chemically bonded to the polymeric materials of the membrane and provide for a water-free separation membrane for separating aliphatically-unsaturated hydrocarbons from mixtures of saturated hydrocarbons.

Metal salts, for example, silver salts such as nitrate or trifluoromethanesulfonate can be applied from water solution to the preformed ion exchange membranes in order to ion exchange the membranes with metal ions. The metal ion exchanged membranes are then dried and plasticized with polyhydric alcohols to complete the membrane according to the invention. Optionally the metal salts can be applied to the membranes simultaneously with the polyhydric alcohols. Residual polyhydric alcohol presence is necessary in the metal ion exchanged membranes in order to achieve suitable separations of the aliphatically-unsaturated hydrocarbons in the water-free membrane. The resulting membrane whether dense or asymmetric with dense zones, provides a membrane for the separation of unsaturated hydrocarbons which have substantial strength for differential pressure applications and provides for reasonably long life utilization. These membranes which are water-free and when fed with, for example a dry, ethylene ethane mixture, exhibits selectivities of from about 8 to about 15 and permeabilities of from about 5 to $10 \times 10^{-10}$. The low volatility of the polyhydric alcohols in the plasticized membrane and the chemically bound metal ions provides membranes having long term performance due to the lack of loss of the polyhydric alcohols from the plasticized membrane.

The preformed membranes which are capable of chemically binding positive metal ions and which are capable of being plasticized by polyhydric alcohols according to the invention are of the essentially solid, water-insoluble, semi-permeable type. These membrane materials are not adequately selective with respect to passage of or permeation by the aliphatically-unsaturated hydrocarbons to preform the desired separations of the components in the mixed hydrocarbon feed stock. However, by introducing the metal ions throughout the preformed membranes which are plasticized by the polyhydric alcohols, the resulting membrane provides a barrier in which the passage of aliphatically-unsaturated hydrocarbons is dominant vs. saturated hydrocarbons. The components of the feed stream must therefore travel through the separation membrane primarily by becoming part of and then becoming separated from the metal ion containing, plasticized membranes. Preferably, the polyhydric alcohols utilized to plasticize the preformed membranes are liquid in nature, thus are capable of plasticizing the entire membrane whether the membrane is a dense membrane, an asymmetric membrane with dense zones, or even coarse membranes. However, the plasticized membrane in the absense of complexing metal ions would result in no or very slight separation of the aliphatically unsaturated hydrocarbons from saturated hydrocarbons. According to the present invention, however, the selectivity of the separation of aliphatically-unsaturated hydrocarbons is greatly increased due to the presence of the complexing metal ions and the polyhydric alcohol plasticized membrane.

In the operations of the invention, the preformed, polyhydric alcohols plasticized, metal ion containing membranes are useful for gaseous, liquid or mixed fluid feed stock separations of aliphatically-unsaturated hydrocarbons from saturated hydrocarbons. The resulting membrane is preferentially thin; however, having sufficient thickness to provide the necessary strengths for differential pressure operations, to allow permeability rates of the unsaturated hydrocarbons while the selectivity is controlled in part by the metal ion concentrations.

The polyhydric alcohol plasticized membranes according to the invention contain sufficient metal ions to form a suitable complex with at least one aliphatically-unsaturated hydrocarbon component of the fluid feed stock. The metal ions readily form the complex upon contact with the unsaturated hydrocarbon components of the fluid feed and, in addition, the complex dissociates back to metal ion and the aliphatically-unsaturated hydrocarbon component of the complex under the conditions which exist at the discharge side of the membrane. The released aliphatically-unsaturated hydrocarbons exit the discharge size of the membrane and can be removed from the vicinity of the discharge side as by a sweep fluid or through the effect of vacuum and/or other means. Thus, the unsaturated hydrocarbons form a metal complex and are decomposed upon their travel through the metal ion containing polyhydric alcohol plasticized membrane. As a result, the material passing through the membrane is more concentrated with respect to at least one aliphatically-unsaturated hydrocarbon component than is present in the feed stock.

The feed fluid need only contain a small amount of aliphatically-unsaturated hydrocarbon, as long as the amount is sufficient so that the unsaturated material to be separated selectively reacts with the metal complex ions to a significant extent, thus at least one of the component of the feed is less reactive or non-reactive with complex forming metal ions. The aliphatically-unsaturated materials of most interests with regard to separation by the method of the present invention and by the membrane of the present invention have from 2 to about 9 carbon atoms per molecule, preferably 2 to about 4 carbon atoms per molecule. The separtion of ethylene or propylene from mixtures of other normally gaseous materials, such as one or more of ethane, methane and propane and hydrogen is of particular importance. Frequently these feed mixtures contain from about 1 to 50 weight percent ethylene, about 0 to 50 weight percent ethane and about 0 to 50 weight percent weight methane.

Metals may be used which serve in the form of metal-containing cations to separate aliphatically-unsaturated hydrocarbons in the feed mixture through the formation of metal complexes of desired properties, and these metals include, for instance, the transition metals of a periodic chart of elements having atomic numbers above 20. Included in these metals are those of the first transition series having atomic numbers from 21 to 29 such as chromium, copper, especially the cuprous ion, and the iron group metals, e.g. nickel and iron. Other of the useful complex forming metals are in the second and third transition series, i.e. having atomic numbers from 39 to 47 or 57 to 79, as well as mercury, particularly as the mercurous ion. Thus, the noble metals such as gold, silver, and the platinum group among which are platinum, palladium, rhodium, ruthenium and osmium are suitable. The useful base metals of the second and third transition series include, for example, molybdenum, tungsten, rhenium and the like are also suitable. Various combinations of these complex-forming metal may also be employed according to the invention, either in the presence or absence of non-metal or non-complexing metal cations.

The preformed membranes which are plasticized by the solution of polyhydric alcohols and metal ions must be capable of chemically binding positive ions and being plasticized by polyhydric alcohols. These membranes can be known as ion exchange membranes such as, for example, halogenated polyolefins with pendant acid groups; sulfonated polymers; carboxylated polymers; polyacrylic acids; and the like.

Facilitated transport membranes frequently show a saturation phenomenon in which selectivity decreases sharply with increasing pressure. The solid membranes according to the invention which are comprised of the polyhydric alcohols, metal ions and plasticized membranes can be operated at pressures of 100 psi differential or higher and still result in reasonable selectivity for aliphatically-unsaturated hydrocarbons. Ion exchange membranes such as cation exchange membranes which can be silver exchanged, dried, equilibrated with a polyhydric alcohol or mixture of polyhydric alcohols and surface dried are suitable for use in the present invention. The solid membrane thus obtained affords good selectivity for example, $\alpha_4 C_2H_4/C_2H_6$ equal to about 8 to about 12 and permeability of $C_2H_4$ equal to 5 to $10 \times 10^{-10}$ in water-free feedstreams. Permeabilities are expressed in cubic centimeters (STP) per square centimeter of membrane area per second per differential partial pressure of one centimeter of mercury across a membrane thickness of 1 cm, $cm^3 \times cm$ (STP)/$cm^2$-sec-cmHg. Unless otherwise noted all permeabilities are reported at ambient temperatures at pressures of approximately 24° C. and 1 atmosphere, respectively.

Another conventional relationship for expressing gas permeation characteristics of a membrane is separation factor. A separation factor $\alpha a/b$, for a membrane for a given pair of gases "a" and "b" is defined as a ratio of the permeability, ($P_a$, of a membrane of thickness "1" for a gas "a" of a gas mixture to the permeability, ($P_b$), of the same membrane to gas "b" of the mixture.

EXAMPLE 1

A commercial cation exchange membrane, Nafion ® 415 (Dupont), a halogenated polyolefin with pendant acid groups, was equilibrated with 2M KOH overnight, rinsed with water, equilibrated with $A_gNO_3$ 6M (aqueous) overnight, rinsed with water, dried and soaked in neat glycerol 48 h. The surface was wiped clean and the membrane was tested in a dry ethylene-ethane mixture at 115 cmHg pressure. The performance observed was:

$$\alpha C_2H_4/C_2H_6 = 10 \quad PC_2H_4 = 6.9 \times 10^{-10}$$

EXAMPLE 2

A control experiment identical to Example 1 except no glycerol treatment. The membrane offered no separation.

EXAMPLE 3

A control experiment identical to Example 1 except no silver exchange.

$$\alpha C_2H_4/C_2H_6 = 2 \quad PC_2H_4 = 1.6 \times 10^{-10}$$

EXAMPLE 4

As in Example 1, exoept the test was performed at 276 cmHg.

$$\alpha C_2H_4/C_2H_6 = 9.6 \quad PC_2H_4 = 4.1 \times 10^{-10}$$

EXAMPLE 5

As in Example 1, except the test was performed at 543 cmHg. Performance after 5 days of continuous operation:

$$\alpha C_2H_4/C_2H_6 = 8.8 \quad PC_2H_4 = 4.5 \times 10^{-10}$$

EXAMPLE 6

As in Example 1 except 1-octanol was used instead of glycerol.

$$\alpha C_2H_4/C_2H_6 = 2.8 \quad PC_2H_4 = 86 \times 10^{-10}$$

The results illustrate that this solvent is thus less suitable then glycerol.

EXAMPLE 7

A Nafion film was converted to the Ag+ form by treating first with KOH followed by water rinsing and equilibration with $AgNo_3$ 5M and rinsing with water again. The film was dried and tested with a 1:1 feed of ethylene/ethane. No selectivity was observed. Selectivity was obtained only upon swelling the film with glycerol as in the other examples.

I claim:

1. An article comprising: a water-free membrane for separating aliphatically-unsaturated hydrocarbons from saturated hydrocarbons including a preformed membrane of polymeric materials for chemically binding positive metal ions which have been ion exchanged with metal ions with the metal ions being chemically bonded to the polymeric materials of the membrane and the membrane has been plasticized by polyhydric alcohols.

2. The water-free membrane according to claim 1 wherein the metal ions are selected from noble metals of the periodic chart.

3. The water-free membrane according to claim 2 wherein the metal ion is silver.

4. The water-free membrane according to claim 1 wherein the aliphatically-unsaturated and saturated hydrocarbons have from one to about nine carbon atoms per molecule.

5. The water-free membrane according to claim 4 wherein the aliphatically-unsaturated and saturated hydrocarbons have from one to about four carbon atoms per molecule.

6. The water-free membrane according to claim 1 which is suitable for separating ethylene from ethane.

7. A process comprising separating a feedstream containing aliphaticaly-unsaturated hydrocarbons and saturated hydrocarbons by contacting the feedstream with a water-free membrane comprised of polymeric materials for chemically binding positive metal ions which have been ion exchanged with metal ions with the metal ions being chemically bonded to the polymeric materials of the membrane and the membrane has been plasticized by polyhydric alcohols; and permeating through the membrane a permeate which has a higher concentration of unsaturated hydrocarbons than in the feedstream.

8. The process according to claim 7 wherein the aliphatically-unsaturated hydrocarbons and saturated hydrocarbons are water-free.

9. The process according to claim 8 wherein the aliphatically-unsaturated hydrocarbons and saturated hydrocarbons have from one to about nine carbon atoms per molecule.

10. The process according to claim 9 wherein ethylene is separated from the group consisting essentially of ethane, methane, and hydrogen.

11. A process comprising forming a water-free membrane for separating aliphatically-unsaturated hydrocarbons from saturated hydrocarbons by forming a membrane of polymeric materials for chemically binding positive metal ions; ion exchanging the polymeric materials of the membrane with metal ions which are chemically bonded to the polymeric materials of the membrane; and plasticizing the formed membrane with polyhydric alcohols.

* * * * *